United States Patent

Müller et al.

[11] Patent Number: 5,128,137
[45] Date of Patent: Jul. 7, 1992

[54] THERAPEUTIC SYSTEM FOR THE TRANSDERMAL OR TRANSMUCOUS ADMINISTRATION OF ACTIVE SUBSTANCES AND THE USE THEREOF

[75] Inventors: Walter Müller; Michael Roreger, both of Neuwied; Heinrich Kindel, Rengsdorf; Peter Bohnenkämper, Warstein; Heike Palm, Ochtendung, all of Fed. Rep. of Germany

[73] Assignee: LTS Lohmann Therapie-Systeme GmbH & Co. KG, Neuwied, Fed. Rep. of Germany

[21] Appl. No.: 475,609

[22] Filed: Feb. 6, 1990

[30] Foreign Application Priority Data

Feb. 9, 1989 [DE] Fed. Rep. of Germany ....... 3903794

[51] Int. Cl.⁵ .............................................. A61F 13/00
[52] U.S. Cl. .................................... 424/449; 424/448
[58] Field of Search .................... 424/449, 448, 447

[56] References Cited

U.S. PATENT DOCUMENTS

| | | | |
|---|---|---|---|
| 4,885,154 | 12/1989 | Cormier et al. | 514/647 |
| 4,906,169 | 3/1990 | Chien et al. | 424/449 |
| 5,000,956 | 3/1991 | Amkraut et al. | 424/448 |
| 5,023,084 | 6/1991 | Chien et al. | 424/449 |

*Primary Examiner*—Thurman K. Page
*Assistant Examiner*—Leon R. Horne
*Attorney, Agent, or Firm*—Sprung Horn Kramer & Woods

[57] ABSTRACT

The present invention relates to a therapeutic system for the transdermal or transmucous administration of active substances via an impermeable backing layer, a reservoir which at least partially comprises active substance, is double-layered and consists of separate parts, and a protective layer, whereby the two reservoir members
 (a) are positioned substantially parallely on top of each other,
 (b) are separated from each other by a removable intermediate layer being impermeable to the active substances of said reservoir members,
 (c) either comprise active substance or auxiliary agents or both at concentrations not corresponding to the distribution equilibrium.

5 Claims, 3 Drawing Sheets

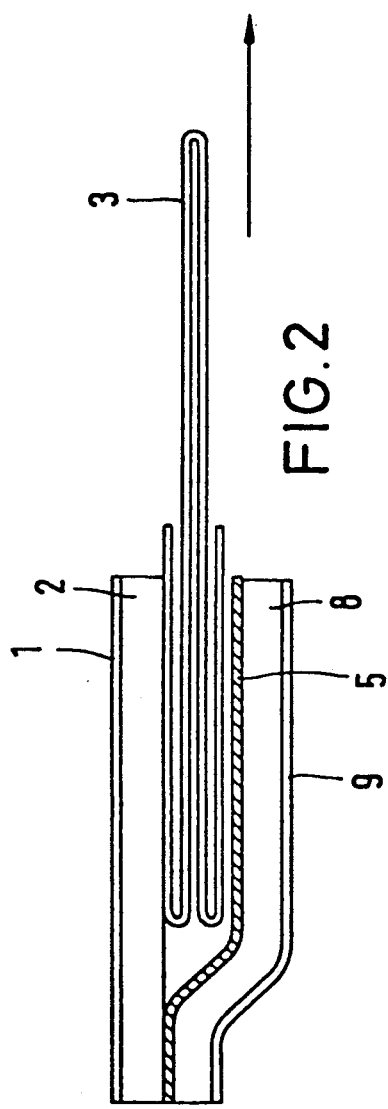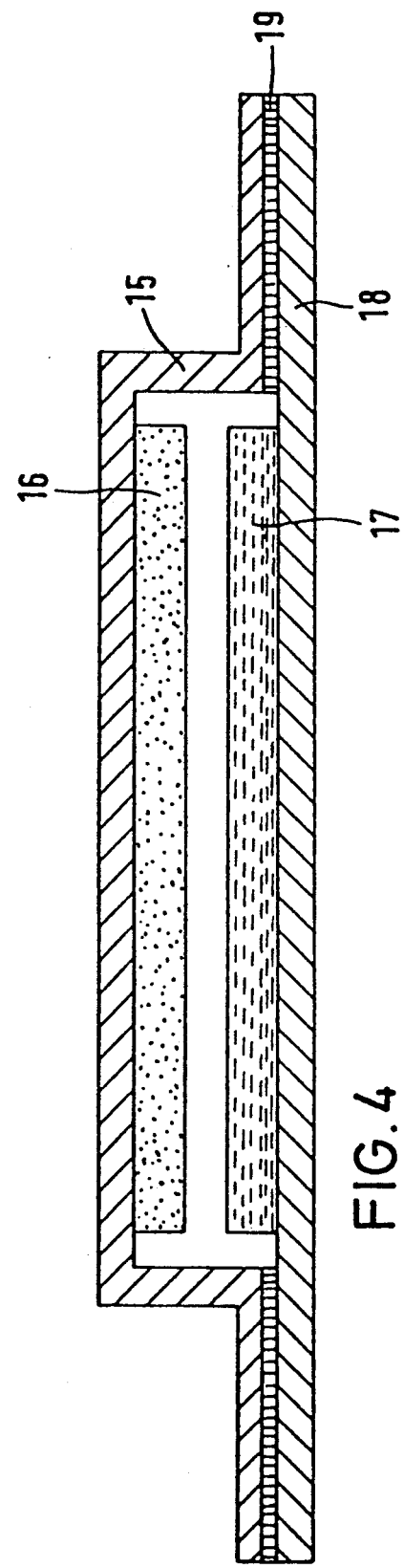

THERAPEUTIC SYSTEM FOR THE TRANSDERMAL OR TRANSMUCOUS ADMINISTRATION OF ACTIVE SUBSTANCES AND THE USE THEREOF

The present invention relates to a therapeutic system for the transdermal or transmucous administration of active substances via an impermeable backing layer, a reservoir which at least partially comprises active substance and which is double-layered and consists of separate parts, and an impermeable and removable protective layer.

In medicine transdermal systems have become established due to their inherent advantages. In the meantime, a number of differently built up systems have been described in literature and come onto the market. For example, in U.S. Pat. No. 3,734,097 (of Alza) a simple, single-layered system is described, and in U.S. Pat. No. 3,598,122 of the same applicant a multi-layered system of a more complicated construction is described, in which additional membranes have controlling functions.

Therapeutic systems are active substance containing devices or forms of administration, respectively, which release one or more pharmaceuticals at a predetermined rate over a fixed period of time to a fixed place of application (see Heilmann "Therapeutische Systeme", Enke publishers, Stuttgart, 1984, page 24). A transdermal therapeutic system releases the active substance via the skin und thus is used on the skin, i.e., topically.

Only in recent times, systems were described in which special manipulations have to be carried out prior to application.

These systems can be divided into two categories. The first category comprises systems in which the active substance is converted into its bioavailable form only immediately prior to use. This is necessary, e.g., if the active substance is unstable in its bioavailable form. The multi-chamber systems described in EP-A 0252459 (Schering Corporation) and in the publication of C. D. Ebert are examples for this category. In this case, the chambers are positioned beside one another in the same plane, and the manipulation to be carried out prior to application is that the liquid chamber contents have to be brought together, e.g., by bursting the walls which separate the chambers.

Systems according to EP-A 0249475 (Alza) belong to the second category. In this case, a drug-free layer is applied on an active substance containing reservoir immediately prior to use, and then applied to the skin with the other side of this layer. The active substance reaches the skin, only when it has passed this drug-free layer. This results in a desired retardation effect which, e.g., is of advantage, if after application in the evening active substance levels are desired in the early morning hours. The manipulations to be carried out are quite complicated particularly in systems according to EP-A 0249475. In this case, the complete surfaces of two areal flexible articles have to be brought into contact so that a laminate is built. This is additionally complicated due to the fact that at least one of these articles has to be self-adhesive. The proposed construction of the system in which reservoir and retardation layer are connected with one another by a kind of hinge renders the manipulation to be carried out relatively difficult, and is a process involving many possible errors. Since transdermal systems administer active substances, this system assembly is not reliably to this respect.

Thus, it was an object of the present invention to develop a system for those and similar cases having an improved reliability with respect to the pharmaceutical, which allows even untrained persons to carry out easily the necessary manipulations, and which may be produced without greater expense. The solution to this object surprisingly was found in the fact that it is possible to position both areal parts of the system parallely on top of each other prior to activiation, if both reservoir members are separated from one another by a removable intermediate layer, and if the active substance and/or auxiliary agent are contained in the reservoir members at concentrations not corresponding to the distribution equilibrium. Thus, in the case of such a system assembly, it is not necessary to connect two separate members with one another orderly, or to carry out manipulations involving a substantial change of the geometric shape of the system.

BRIEF DESCRIPTION OF THE DRAWINGS

Details of the invention are illustrated by the figures by way of example.

Figure 1:
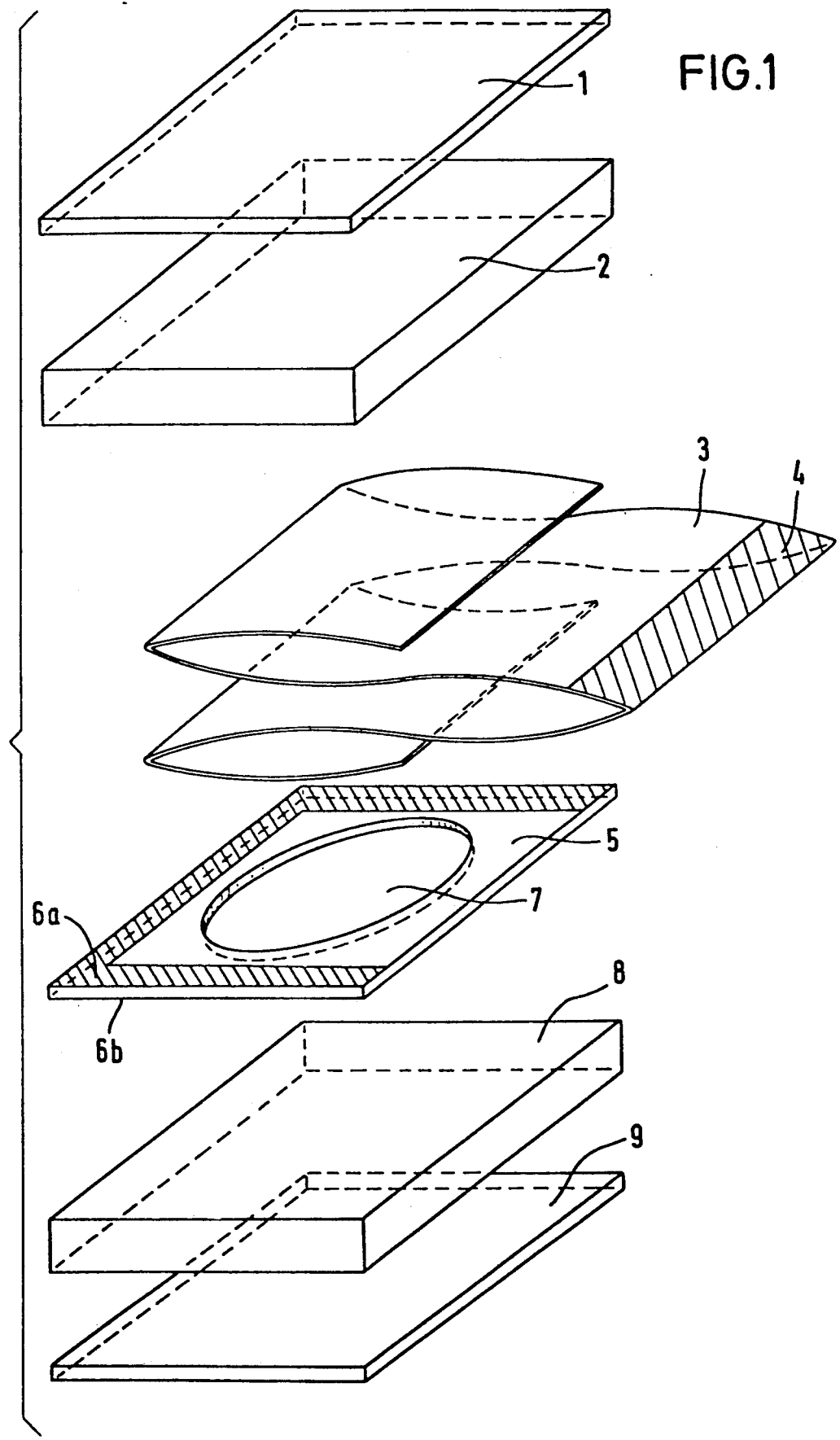
FIG. 1 shows a system according to the present invention. It consists of a carrier foil (1) being impermeable to the content of the upper reservoir member (2), the upper reservoir member (2), an extractable separating foil (3) provided with a touch slip (4) said foil covering aperture (7) of mask (5), perforated mask (5) having a recess (7), the lower member of the reservoir (8), and a pull foil (9) which is impermeable to the content of the lower reservoir member (8) and which has to be removed prior to use.

Perforated mask (5) is in contact with the upper reservoir via its contact surface (6a), shown hatched, and with the lower reservoir (8) via its contact surface (6b). Thus, contact surface (6a) corresponds to the total surface, i.e., to the rectangular surface of perforated mask (5) minus the recess area (7). As a matter of fact, perforated mask (5) as well as separating foil (3) are impermeable to the contents of both reservoir members; this does not apply to recess (7). It is a precondition in the shown assembly that both reservoir members, which are separated prior to application, are self-adhesive. The cohesion of the system is then guaranteed in that reservoir member (8) completely glues on contact surface (6b), and reservoir member (2) glues on the hatched surface (6a) of perforated mask (5).

If these surfaces of the separated reservoir members are not self-adhesive, it is not difficult to provide them either completely or only on the relevant parts with an additional adhesive film. The same applies to the contact surface of the upper reservoir member with carrier foil (1), and to that side of the lower reservoir member (8) facing the skin after application.

As a matter of fact, aperture (7) of perforated mask (5) may also be of other shape than a circular one, and in particular suitable is a U-shape to enlarge the contact area between the reservoir members to be combined.

The system is activated by pulling out the specially folded and siliconized foil (3). This particular folding allows the easy pulling out, if both reservoir members are self-adhesive, since the forces are guided in such a way that the force vector is in vertical line to the plane of the reservoir members. This is illustrated in FIG. 2 which shows a view on the narrow edge of the system which has been cut in the middle. A foil similarly folded is used in EP-A 0241119 (American Home Products Corporation). This foil is used to provide an active substance containing reservoir, which is only storable in an aluminized packing, with a non-aluminized carrier foil for the transdermal application immediately prior to use. Thus, the purpose is completely different, and in addition the possibility to use a foil folded in such a way for the easy in-situ production of laminates was not realized.

In principle, all siliconizable flexible materials are suitable for preparing the separating foil. In order to guarantee an absolute impermeability even for very small molecules, a polymer-metal-composite foil may be used.

Figure 3:
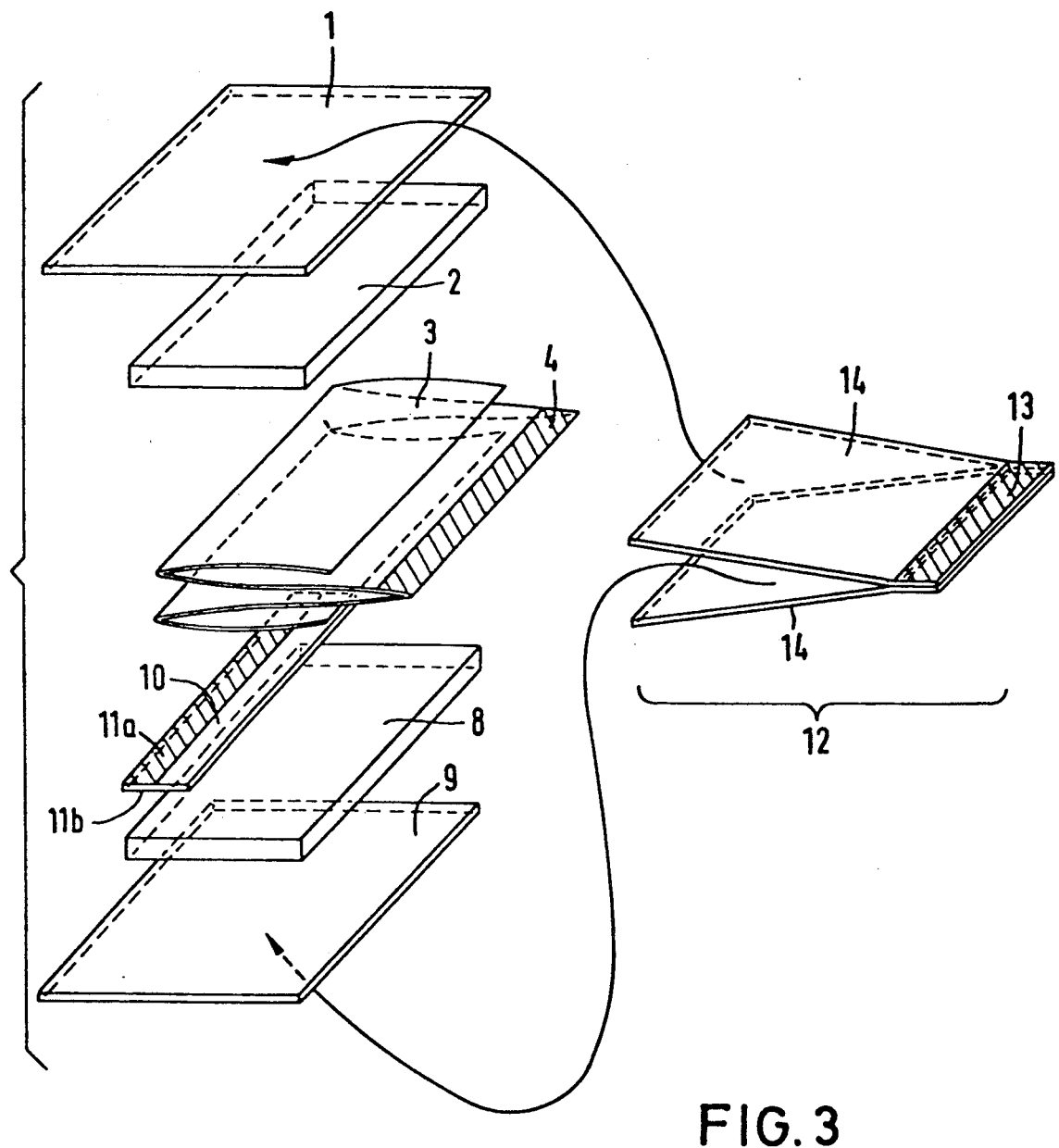

FIG. 3 shows a system which is built up identical in principle, however, the perforated mask (5) (FIG. 1) is reduced to a strip (10) the upper surface (11a) of which contacts upper reservoir member (2) and the lower surface (11b) of which contacts the lower reservoir member. The advantage of this system assembly is the fact that the contact surface between reservoir members (2) and (8), which are to be combined, is very large, and in addition it can be produced more easily. If a very flexible carrier foil (1) is used, a lateral displaced lamination of reservoir members (2) and (8) may occur in case of very inadvertent handling. In order to avoid this, lamination aid (12) is used. The system is positioned between the surfaces (14) of lamination aid (12), and the extractable separating foil (3) is connected on surface (13) with the lamination aid. By way of pulling out the system from the lamination aid the complete system is produced, whereby slight pressure on surfaces (14) supports the lamination process and effectively prevents lateral displacement of the lamination.

Instead of perforated mask (5, 10) reservoir members (2, 8) may contact via a removable joint between backing layer or separating foil (1), respectively, and removable protective foil (9), whereby backing layer (1) and protective layer (9) at least on one side extend the reservoir surfaces (2, 8).

Since this lamination aid prevents the application of the system on the skin without prior preparation of the total laminate, it is suitable in this sense in a system assembly as shown in FIG. 1 as well, in order to avoid that the lamination process is forgotten unintentionally.

Thus, an advantage of the system assembly according to FIG. 1 is pointed out. That is to say, this assembly, in contrast to all other systems described up to now, allows the production of the total laminate, even after glueing to the skin at any time.

FIG. 4 shows a system in which the intermediate layer is built by a slit filled with gas. On the bottom of a deep drawing mould (15) optionally siliconized on its inner side, reservoir member (16) is positioned which after application is in contact with the skin. The upper reservoir member (17) is located on carrier foil (18) being impermeable to the contents of (17). Carrier foil (18) is adhesively bonded with deep drawing mould (15) on area (19). However, reservoir member (17) may have the same dimensions as carrier foil (18) so that (17) is in contact with the deep drawing mould via area (19). Prior to application, the contact between laminate parts (16) and (17) is created by mechanical pressure on the deep drawing mould, and thus the complete system is obtained. In order to apply this system to the skin, it is only necessary to remove the deep drawing mould, which in this connection corresponds to pull foil (9) (FIGS. 3 and 4). In all system arrangements described, the reservoir members (2) and (8) may be built up as complicated as desired. In particular, the incorporation of additional diffusion regulating membranes can prove suitable.

| List of reference numbers | |
|---|---|
| Impermeable backing layer or carrier foil, respectively | 1, 18 |
| Upper reservoir member averted from the skin after application | 2, 17 |
| Extractable separating foil | 3 |
| Touch slip of separating foil | 4 |
| Perforated mask | 5, 10 |
| Contact surface between perforated mask and upper reservoir member | 6a, 11a |
| Contact surface between perforated mask and lower reservoir member | 6b, 11b |
| Aperture of the perforated mask | 7 |
| Lower reservoir member facing the skin after application | 8, 16 |
| Removable protective foil | 9 |
| Lamination aid | 12 |
| Connecting surface between separating foil (3) and lamination aid (12) | 13 |
| Press areas of lamination aid | 14 |
| Deep drawing mould siliconized internally | 15 |
| Adhesive surface connection between deep drawing mould (15) and carrier foil (18) | 19 |

We claim:

1. In a therapeutic system for the transdermal or transmucous administration of an active substance comprising an impermeable backing layer, a reservoir which at least partially contains the active substance, which is double-layered and which comprises separate members, and a protective layer, wherein the two reservoir members (a) are positioned substantially parallel on top of one another, (b) are separated from each other by a removable intermediate layer which is impermeable to the active substance of said reservoir members, and (c) either contain active subtance or an auxiliary agent or both at concentrations not corresponding to the ultimate distribution equilibrium, the improvement which comprises bonding the two reservoir members to one another via a mask, and positioning the intermediate layer (b) between one reservoir member and said mask, said layer (b) being formed of folded foils which at least partially extend laterally beyond the surfaces of the reservoir members.

2. In a therapeutic system for the transdermal or transmucous administration of an active substance comprising an impermeable backing layer, a reservoir which at least partially contains the active substance, which is double-layered and which comprises separate members, and a protective layer, wherein the two reservoir members (a) are positioned substantially parallel on top of one another, (b) are separated from each other by a removable intermediate layer which is impermeable to the active substance of said reservoir members, and (c) either contain active substance or an auxiliary agent or both at concentrations not corresponding to the ultimate distribution equilibrium, the improvement which comprises employing reservoir members which are self-adhesive, the intermediate layer of (b) being filled with gas.

3. A therapeutic system according to claim 1, wherein the intermediate layer (b) comprises a siliconized, flexible material.

4. A therapeutic system according to claim 1, wherein the intermediate layer (b) comprises a polymer-metal-composite foil.

5. A therapeutic system according to claim 1, wherein the mask is formed as a strip joining the longitudinal edges of the two reservoir members.

* * * * *